(12) United States Patent
Kobayashi

(10) Patent No.: US 7,388,659 B2
(45) Date of Patent: Jun. 17, 2008

(54) PARTICLE INSPECTION APPARATUS AND METHOD, EXPOSURE APPARATUS, AND DEVICE MANUFACTURING METHOD

(75) Inventor: Yoichiro Kobayashi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 139 days.

(21) Appl. No.: 11/359,431

(22) Filed: Feb. 23, 2006

(65) Prior Publication Data

US 2006/0238752 A1   Oct. 26, 2006

(30) Foreign Application Priority Data

Apr. 20, 2005   (JP)   .............................. 2005-122945

(51) Int. Cl.
*G01N 21/00*   (2006.01)

(52) U.S. Cl. .................................. 356/237.3; 356/243.4

(58) Field of Classification Search .... 356/237.1–237.5
See application file for complete search history.

(56) References Cited

U.S. PATENT DOCUMENTS

| | | | | |
|---|---|---|---|---|
| 3,799,679 A | * | 3/1974 | Simko | ........................ 356/431 |
| 4,568,835 A | | 2/1986 | Imamura et al. | ............. 250/572 |
| 4,669,875 A | * | 6/1987 | Shiba et al. | .............. 356/237.3 |
| 4,831,274 A | | 5/1989 | Kohno et al. | ................. 250/563 |
| 4,988,204 A | * | 1/1991 | Sakaguchi et al. | .......... 356/430 |
| 5,365,330 A | | 11/1994 | Hagiwara | ................... 356/237 |
| 5,473,426 A | | 12/1995 | Hayano et al. | .............. 356/237 |
| 5,581,348 A | | 12/1996 | Miura et al. | ................. 356/237 |
| 5,585,918 A | | 12/1996 | Takeuchi et al. | ............. 356/237 |
| 5,652,657 A | | 7/1997 | Yoshii et al. | ................. 356/394 |
| 5,963,316 A | * | 10/1999 | Miura et al. | ............. 356/237.3 |
| 6,313,913 B1 | | 11/2001 | Nakagawa et al. | ........ 356/237.2 |
| 6,778,285 B1 | | 8/2004 | Nguyen et al. | .............. 356/630 |

FOREIGN PATENT DOCUMENTS

| | | |
|---|---|---|
| JP | 58-79240 | 5/1983 |
| JP | 58-139113 | 8/1983 |
| JP | 3-217843 | 9/1991 |
| JP | 4-62457 | 2/1992 |
| JP | 6-258237 | 9/1994 |
| JP | 7-43312 | 2/1995 |
| JP | 2004-53972 | 2/2004 |

OTHER PUBLICATIONS

European Search Report and Examination Report dated Aug. 3, 2006, issued in corresponding European patent application No. EP 06 00 3289, forwarded in a Communication dated Aug. 22, 2006.
Japanese Office Action dated Feb. 1, 2008, issued in corresponding Japanese patent application No. 2005-122945.

* cited by examiner

*Primary Examiner*—Hoa Q Pham
(74) *Attorney, Agent, or Firm*—Fitzpatrick, Cella, Harper & Scinto

(57) ABSTRACT

An inspection apparatus for inspecting a surface of an object for a particle. The apparatus includes an irradiator configured to irradiate the surface with inspection light, a first detector configured to detect light scattered at the surface, a shield configured to limit an irradiation region of the inspection light emitted by said irradiator within a limited region of the surface, and a field stop arranged between the detector and the surface and having an aperture which allows the light scattered at an edge portion of an end face of the object to pass through, in which the light passing through the aperture is detected.

9 Claims, 16 Drawing Sheets

SHIELD USING FLAT PLATE

SAWTOOTHED SHIELD

F I G. 15
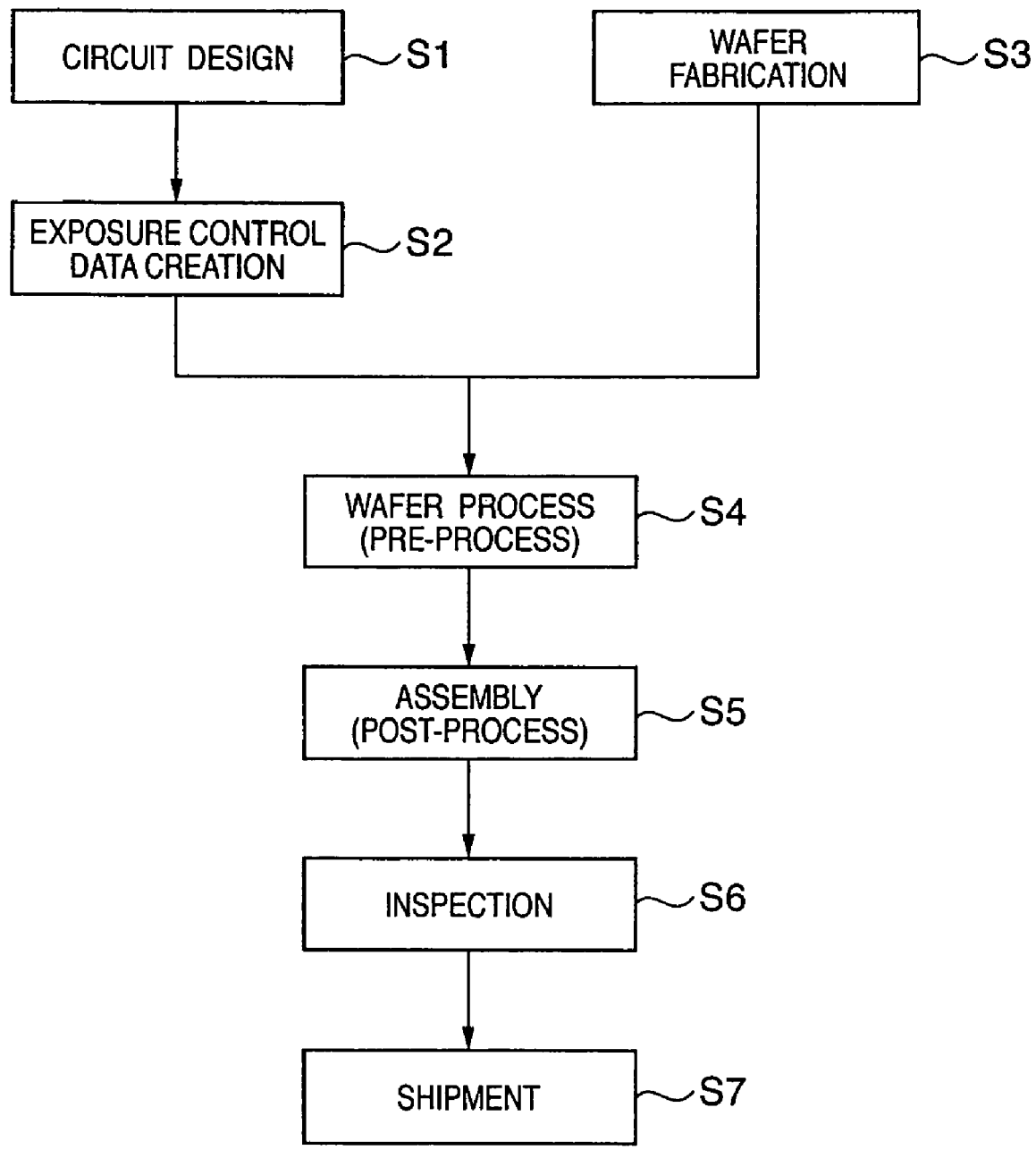

PARTICLE INSPECTION APPARATUS AND METHOD, EXPOSURE APPARATUS, AND DEVICE MANUFACTURING METHOD

FIELD OF THE INVENTION

The present invention relates to a particle inspection technique for inspecting the surface of an object for a particle, and an exposure technique using the particle inspection technique.

BACKGROUND OF THE INVENTION

In manufacturing a semiconductor element formed from a micropattern, such as an LSI or a VLSI, a reduction projection exposure apparatus is used to form, by exposure, a circuit pattern drawn on a reticle or a mask by reducing and projecting it onto a wafer coated with a photosensitive agent. Along with an increase in mounting density of a semiconductor element, further micropatterning is required. The exposure apparatus takes a measure to implement micropatterning at the same time as the development of a resist process.

Unfortunately, if a particle such as dust adheres to the substrate surface in pattern transfer, the particle is also transferred in the circuit pattern, resulting in a large decrease in manufacturing yield of an IC or LSI. For this reason, a mask or reticle generally has a pattern protective member, called a pellicle, consisting of transparent thin films, which are made of cellulose nitrate and have a thickness of about 1 μm. This prevents a particle such as dust from adhering to the reticle pattern surface.

If a particle adheres to the reticle blank surface or a pellicle surface spaced apart from the reticle pattern surface, the particle is not transferred onto a wafer. However, a defocused image of the particle adhering to the above-mentioned surface may possibly be transferred, so the light amount varies on the wafer, resulting in unsatisfactory exposure.

To solve this problem, the presence/absence of a particle on a reticle (blank surface) or a pellicle must inevitably be detected before and/or after exposure in manufacturing an IC or LSI. A general method takes advantage of a nature in which a particle diffuses light isotropically. For example, parallel light beams are collectively applied to the inspection surface region obliquely from above. Scattered light from a particle is applied onto a one-dimensional image sensor (sensor array) by a microlens array of a refractive index distribution type to image the particle. Then, the inspection surface is inspected to detect the presence/absence of a particle (to be referred to as a foreign particle or contaminant hereinafter).

FIG. 12 is a view showing an outline of the structure of a particle inspection apparatus. A reticle 1 and pellicle 2 (not shown) as inspection objects are held on an inspection table 6. An inspection light forming unit (also to be referred to as an irradiator) 7 forms inspection light and irradiates an inspection object with it. A reticle side detector 3 faces the reticle 1 and detects inspection light applied to the reticle 1. A pellicle side detector 4 faces the pellicle 2 and detects inspection light applied to the pellicle 2.

The inspection light forming unit 7 scans the reticle side detector 3 and pellicle-side detector 4 in the direction of an arrow (x direction) with respect to an inspection object to inspect the entire surface of the inspection object for a particle.

FIG. 13 is a side view of FIG. 12 when viewed from the x direction, and a structure on the pellicle 2 side is omitted.

Referring to FIG. 13, the inspection light forming unit 7 collectively applies inspection light beams 14a as parallel light beams to the reticle 1. The applied inspection light beams are detected by the detector 3 to detect a particle.

At this time, part of the inspection light beams 14a emitted from the inspection light forming unit 7 comes from an edge portion 1a (end face portion) of the reticle 1 and enters the reticle 1. The entered inspection light is sometimes diffracted by a pattern 20 drawn on the reticle 1 to generate a diffraction light beam 21. When the diffraction light beam 21 strikes the detector 3, it is erroneously detected as scattered light from a particle. This disables accurate particle detection.

As disclosed in Japanese Patent Laid Open No. 58-79240, a shield member is conventionally arranged in a direction in which scattered light from a particle is not shielded while shielding stray light such as diffraction light in a detector. However, a direction in which diffraction light is generated depends on the pattern of a reticle, so it is difficult to shield diffraction light in every state.

SUMMARY OF THE INVENTION

The present invention has been made in consideration of the above background, and has as its exemplary object to provide a novel technique for realizing particle inspection with high accuracy.

In order to achieve the above object, according to the present invention, there is provided an inspection apparatus for inspecting a surface of an object for a particle, comprising an irradiator configured to irradiate the surface with inspection light, a first detector configured to detect light scattered at the surface, and a shield configured to limit an irradiation region of the inspection light emitted by the irradiator within a limited region of the surface.

According to the present invention, there is also provided an inspection method of inspecting a surface of an object for a particle, comprising an emission step of emitting inspection light, a shield step of shielding the inspection light with a shield to limit an irradiation region of the emitted inspection light within a limited region of the surface, and a first detection step of detecting light scattered at the surface irradiated with the shielded inspection light.

The present invention can also be applied to an exposure apparatus for exposing a substrate to light via a reticle having the above inspection apparatus, and a method of manufacturing a device, comprising steps of exposing a substrate to light via a reticle using an exposure apparatus as defined above, developing the exposed substrate, and processing the developed substrate to manufacture the device.

The present invention makes it possible to provide a novel technique for realizing particle inspection with high accuracy.

Other objects and advantages besides those discussed above shall be apparent to those skilled in the art from the description of a preferred embodiment of the invention which follows. In the description, reference is made to the accompanying drawings, which form a part thereof, and which illustrate an example of the invention. Such an example, however, is not exhaustive of the various embodiments of the invention, and, therefore, reference is made to the claims which follow the description for determining the scope of the invention.

BRIEF DESCRIPTION OF THE DRAWINGS

FIG. 15 is a flowchart showing the manufacturing flow of a microdevice; and

DETAILED DESCRIPTION OF THE PREFERRED EMBODIMENTS

Embodiments of the present invention will be described below in detail with reference to the accompanying drawings.

Note that the embodiments to be described hereinafter are examples as implementation means of the present invention, and should be appropriately modified or changed in accordance with various conditions and the structure of an apparatus to which the present invention is applied.

First Embodiment

Figure 1:
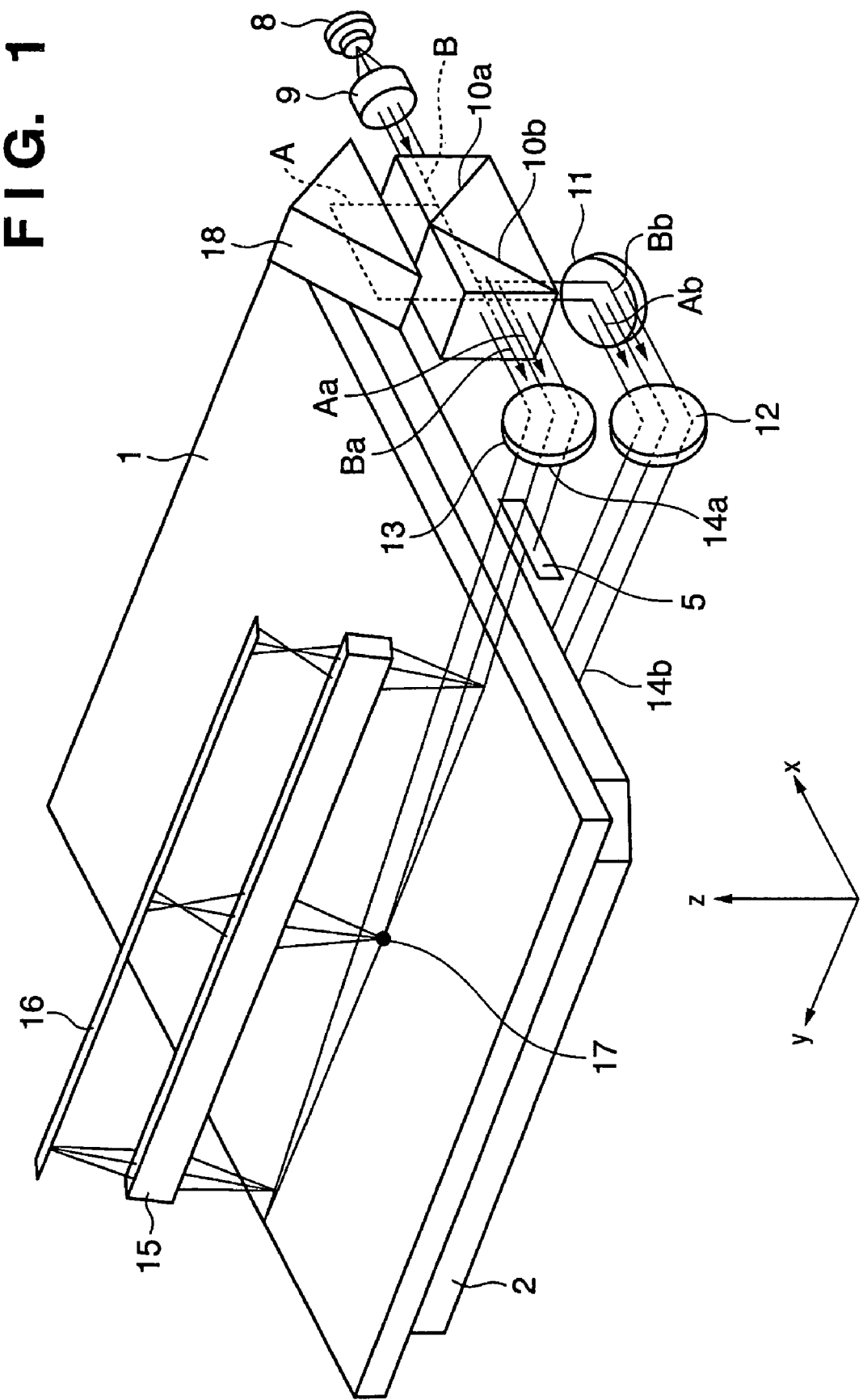
FIG. 1 is a view showing an outline of the structure of a particle inspection apparatus according to the first embodiment of the present invention.

FIG. 1 is a view showing an outline of the structure of a particle inspection apparatus according to the first embodiment of the present invention.

As shown in FIG. 1, a laser beam emitted from a laser diode 8 is converted into a parallel light beam by a collimator lens 9. The collimated laser beam is split by a beam splitter (half mirror) 10a into two light beams A and B having almost the same intensity with each other. A transmitted light beam B transmitted through the beam splitter 10a is applied to a beam splitter 10b. A reflected light beam A reflected by the beam splitter 10b is applied to a cube corner reflector 18.

The cube corner reflector 18 is arranged to be shifted from the beam splitters 10a and 10b in the x direction by a predetermined amount L/2. The light beams A and B are combined in the beam splitter 10b. After that, light beams Aa and Ba emitted from the beam splitter 10b in the x direction become parallel with each other, and form a shape in which the centers of the two light beams are spaced by a distance L.

Since the beam splitter 10b is a half mirror, it emits light beams Ab and Bb in the z direction, the centers of which are spaced by the distance L.

Combined light beams (Aa+Ba) and (Ab+Bb) are applied, as inspection light beams 14a and 14b in two directions, to the upper surface (inspection surface) of a reticle 1 and the lower surface (inspection surface) of a pellicle 2, respectively. The inspection light beams 14a and 14b formed into a vertically long shape by the beam splitters 10a and 10b are obliquely applied to the surfaces of the reticle 1 and pellicle 2 at a predetermined angle by reflectors (mirrors) 11, 12, and 13, thus forming almost uniform slit light on the inspection surfaces.

Figure 12:
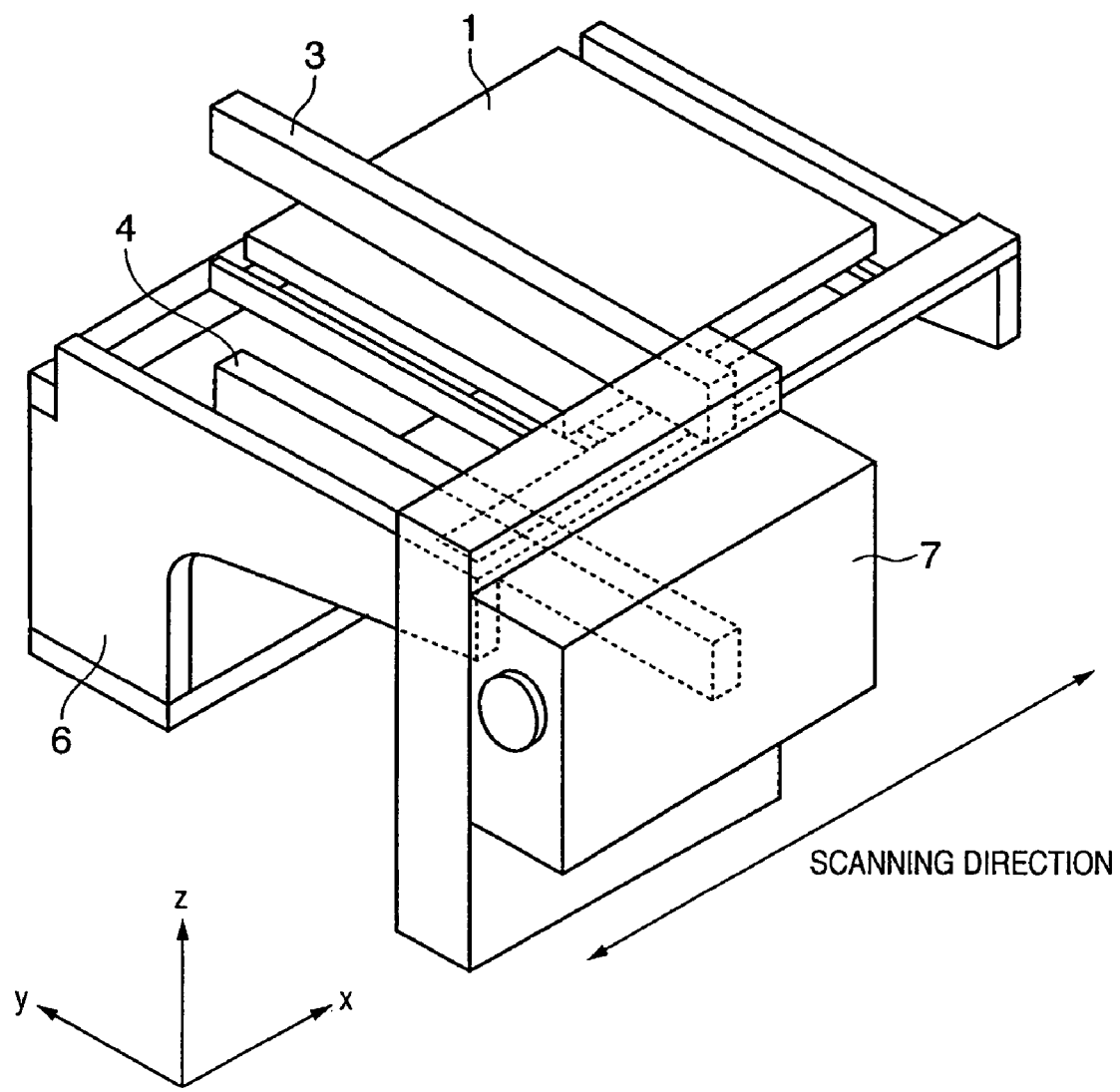
FIG. 12 is a view showing a particle inspection apparatus.

As described with reference to FIG. 12, detectors 3 and 4 and inspection light forming unit 7 are scanned in the x direction with respect to the reticle 1 and pellicle 2 to inspect the entire inspection surface of the inspection object for a particle. If a particle 17 is present in the irradiation region of inspection light, scattered light is generated from the particle. The scattered light is imaged on a line sensor 16 by lens array 15 arranged along the irradiation region of inspection light.

A characteristic feature of this embodiment is that a shield (plate) 5 is so arranged as to limit the irradiation range of inspection light such that the inspection light 14a is prevented from striking the edge portion of the inspection object.

Figure 2:
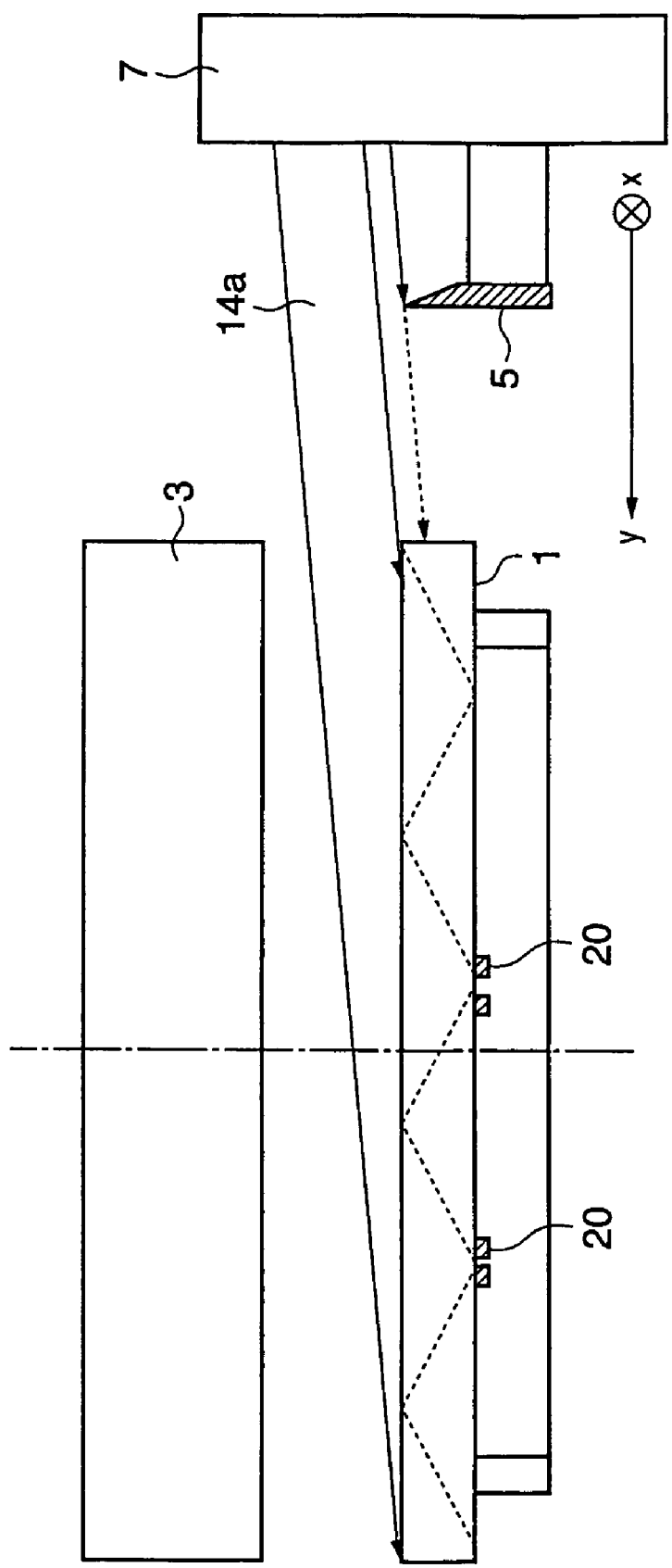
FIG. 2 is a side view of FIG. 1 when viewed from the x direction.

FIG. 2 is a side view of FIG. 1 when viewed from the x direction, and a structure on the pellicle 2 side is omitted.

As shown in FIG. 2, the shield 5 is arranged between the reticle 1 and inspection light forming unit 7. The shield 5 serves to shield inspection light over the entire inspection surface when it moves by scanning together with the inspection light forming unit 7.

Figure 13:
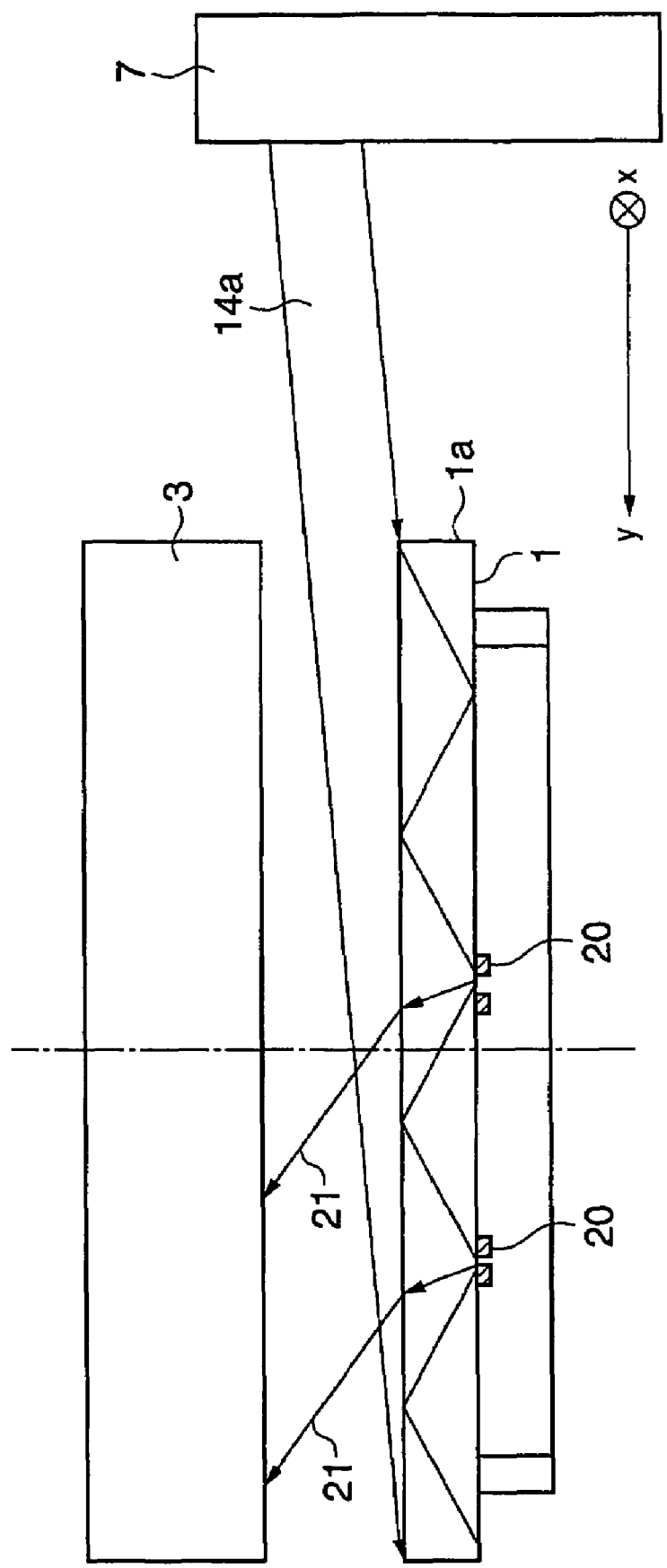
FIG. 13 is a side view of FIG. 12 when viewed from the x direction.

Of inspection light beams 14a emitted from the inspection light forming unit 7, an inspection light beam 14a applied to an edge portion 1a of the reticle 1 is shielded by the shield 5 so as not to generate a diffracted light beam 21 due to a pattern 20 drawn on the reticle 1, as described with reference to FIG. 13. More specifically, since the sensitivity of a detector to the diffracted light beam 21 can be set low, the intensity (light amount) of inspection light can be relatively high. This makes it possible to detect scattered light by a smaller particle, thus realizing highly accurate particle inspection.

Figure 3:
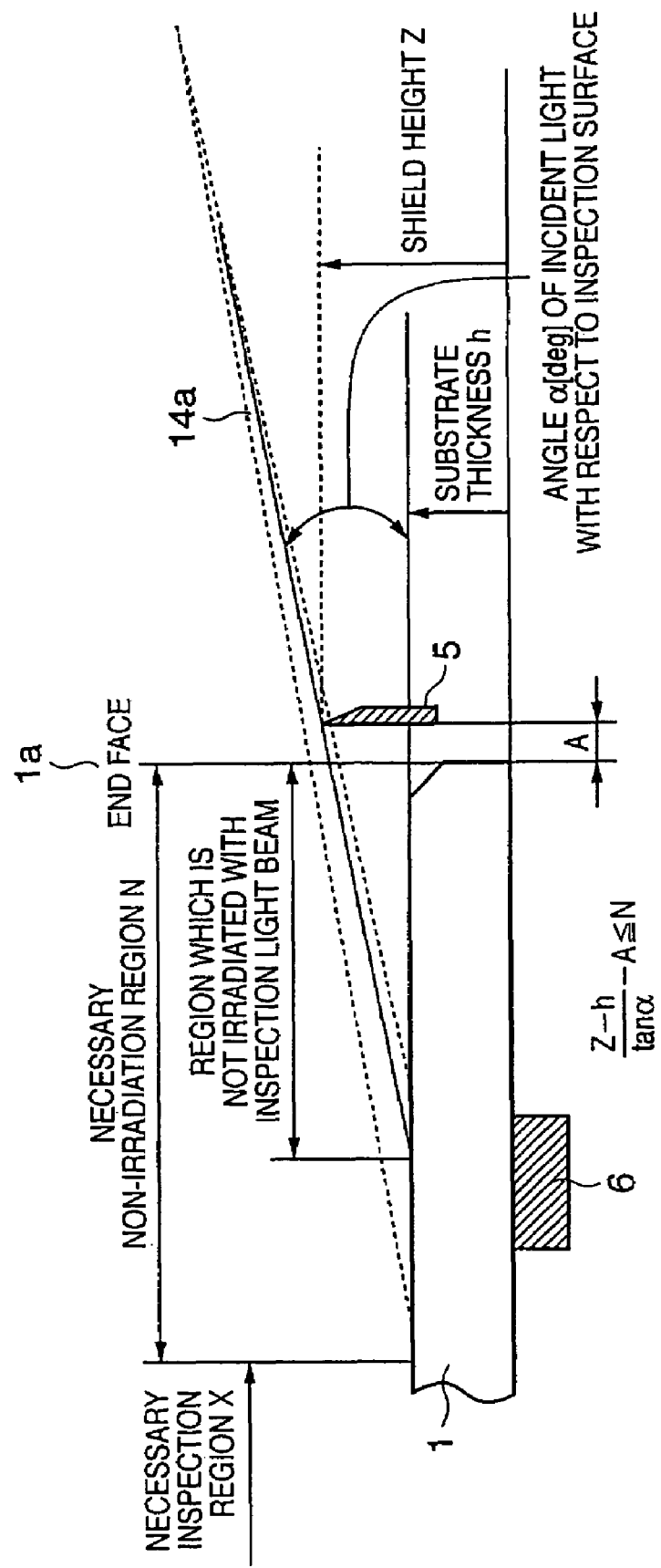
FIG. 3 is a side view showing the positional relationship between an inspection light beam and a shield when viewed from the x direction.

FIG. 3 is a side view showing the positional relationship between the inspection light beam 14a and the shield 5 when viewed from the x direction.

Referring to FIG. 3, let X be a necessary inspection region, and N be a non-irradiation region necessary not to irradiate the end face 1a of the reticle 1. Letting A be the distance from the end face 1a to the shield 5, Z be the height from an inspection table 6, h be the thickness of the reticle 1, and α be the angle [deg] of the incident inspection light beam 14a with respect to the reticle surface, the shield 5 is arranged to satisfy a condition to be obtained by a geometrical relationship:

$$(Z-h)/\tan \alpha - A \leq N.$$

Figure 4:
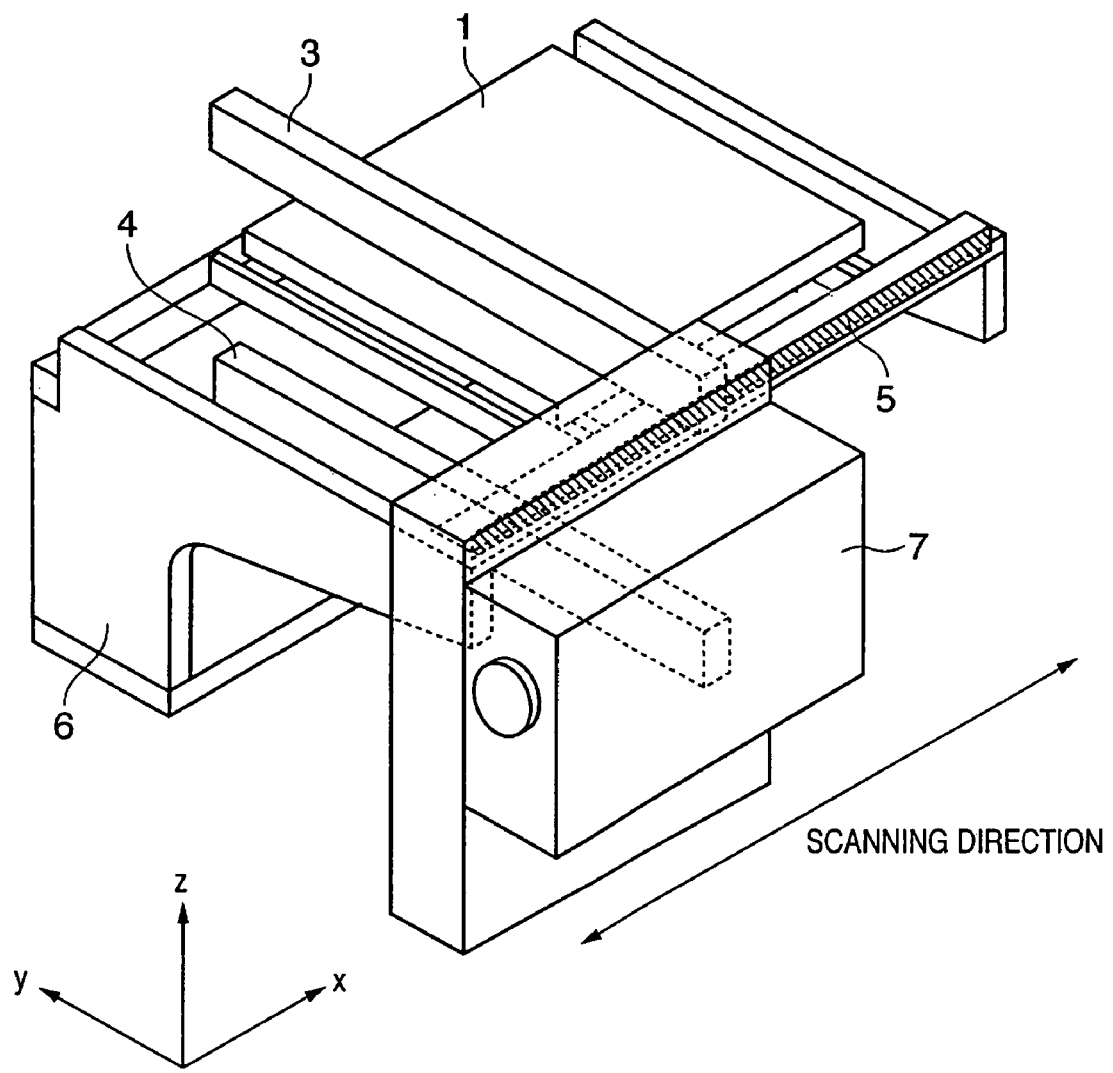
FIG. 4 is a view showing a particle inspection apparatus as a modification of the first embodiment.

In this embodiment, the shield 5 is arranged on the inspection light forming unit 7 to be scanned. However, the shield 5 may be arranged on the inspection table 6 to extend over the scanning direction, as illustrated in FIG. 4. The edge portion of the shield 5 is more preferably sharp like the edge of a knife, and should be closer to the reticle 1. A low-reflecting member is more preferable to reduce flare from the shield.

Note that the shield 5 of the inspection light 14a applied to the reticle 1 has been described in this embodiment. However, the shield 5 can be similarly used for the inspection light 14b applied to the pellicle 2.

Second Embodiment

Figure 5:
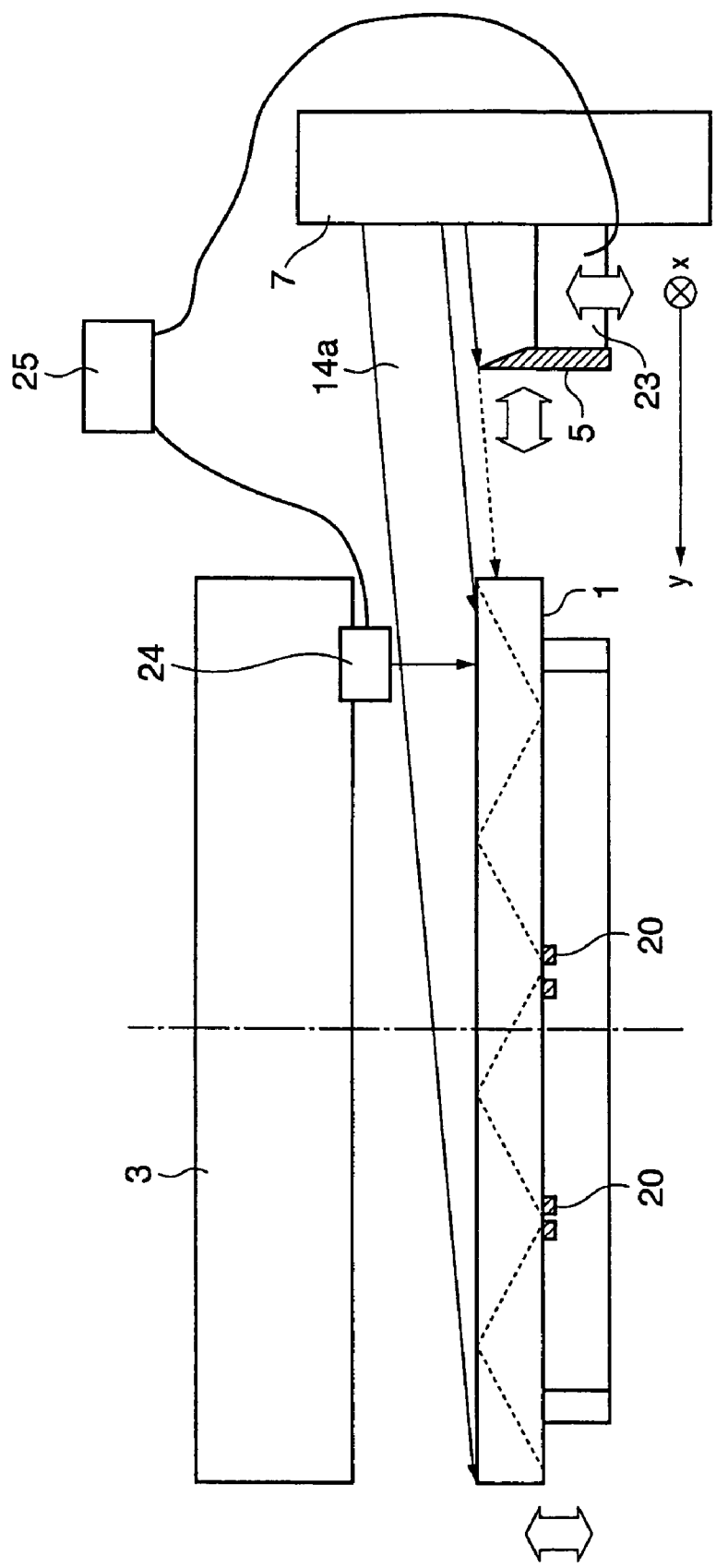
FIG. 5 is a side view showing an outline of the structure of a particle inspection apparatus according to the second embodiment when viewed from the x direction.

FIG. 5 is a side view showing an outline of the structure of a particle inspection apparatus according to the second embodiment when viewed from the x direction, and a structure on the pellicle 2 side is omitted.

In the second embodiment, a position measurement mechanism 24 is arranged to measure the position (height to a detector 3) of the inspection surface of a reticle 1.

As shown in FIG. 5, a shield 5 is attached to an inspection light forming unit 7 through a position adjustment mechanism 23 consisting of actuators such as a motor. A controller 25 drives the position adjustment mechanism 23 to control the position and orientation (with respect to the detector and edge portion) of the shield 5. Information about the position of the inspection surface measured by the position measurement mechanism 24 is sent to the controller 25. Then, the position of the shield 5 is corrected by driving the position adjustment mechanism 23 such that the positions of the inspection surface and shield 5 satisfy the above condition.

The position measurement mechanism 24 moves by scanning together with the inspection light forming unit 7, thereby inspecting a particle while correcting the position of the shield 5. Note that the shield 5 may be movable in the horizontal direction instead of the vertical direction to execute position adjustment. If the angle of an incident inspection light beam 14a with respect to the reticle surface is acute (small), the inspection light beam 14a is less sensitive to position adjustment in the horizontal direction than in the vertical direction (that is, a variation in intensities of inspection light beams 14a is small in the horizontal direction). This makes it possible to simplify the structure of the position adjustment mechanism 23. The reticle 1 may be relatively displaced with respect to the shield 5 by using a stage apparatus, or the like.

Third Embodiment

Figure 6:
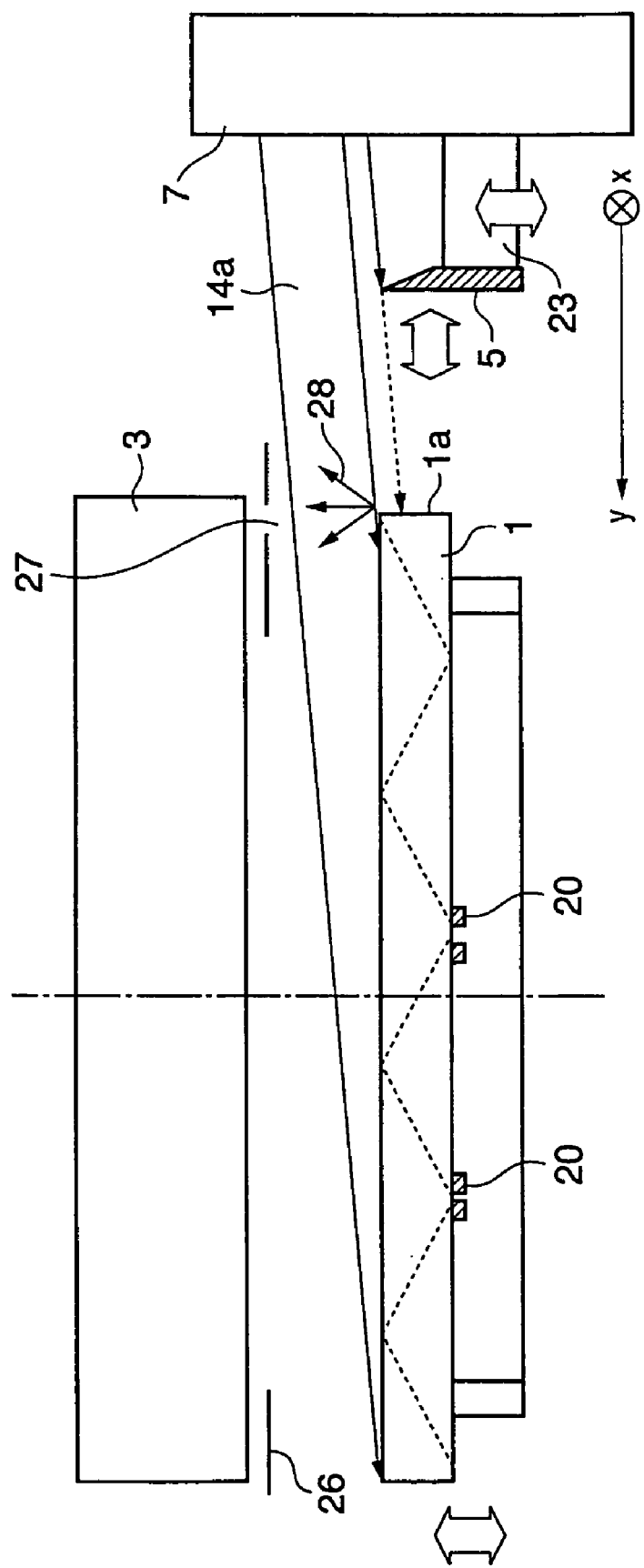
FIG. 6 is a side view showing an outline of the structure of a particle inspection apparatus according to the third embodiment when viewed from the x direction.

FIG. 6 is a side view showing an outline of the structure of a particle inspection apparatus according to the third embodiment when viewed from the x direction, and a structure on the pellicle 2 side is omitted.

In the second embodiment, the position measurement mechanism 24 for measuring the position of an inspection surface is arranged to correct the position of the shield 5 in accordance with the height of the inspection surface. By contrast, in this embodiment, a detector 3 detects inspection light which diffuses on an end face 1a of a reticle 1, and the position of a shield 5 is adjusted to prevent an inspection light beam 14a from striking the edge portion of the end face 1a.

As shown in FIG. 6, a field stop 26 is arranged between the detector 3 and inspection surface to limit an inspection region. This prevents the detector 3 from detecting inspection light beams 28 which scatter on the edge portion of the end face 1a. In this embodiment, an aperture 27 is separately formed near the end face to detect the inspection light beams 28 which scatter on the edge portion of the end face 1a. The aperture 27 allows a line sensor (not shown) arranged in the detector 3 to detect scattered light on the edge portion. The detected light amount information is sent to a controller (not shown) to cause a position adjustment mechanism 23 to correct the position of the shield 5. The reticle 1 may be relatively displaced with respect to the shield 5.

The intensity of scattered light on the edge portion is higher than that of scattered light by a particle. For this reason, it is possible to adjust the size of the aperture 27 to limit the incident light amount, thereby preventing saturation of charges accumulated in a sensor.

Fourth Embodiment

Figure 7:
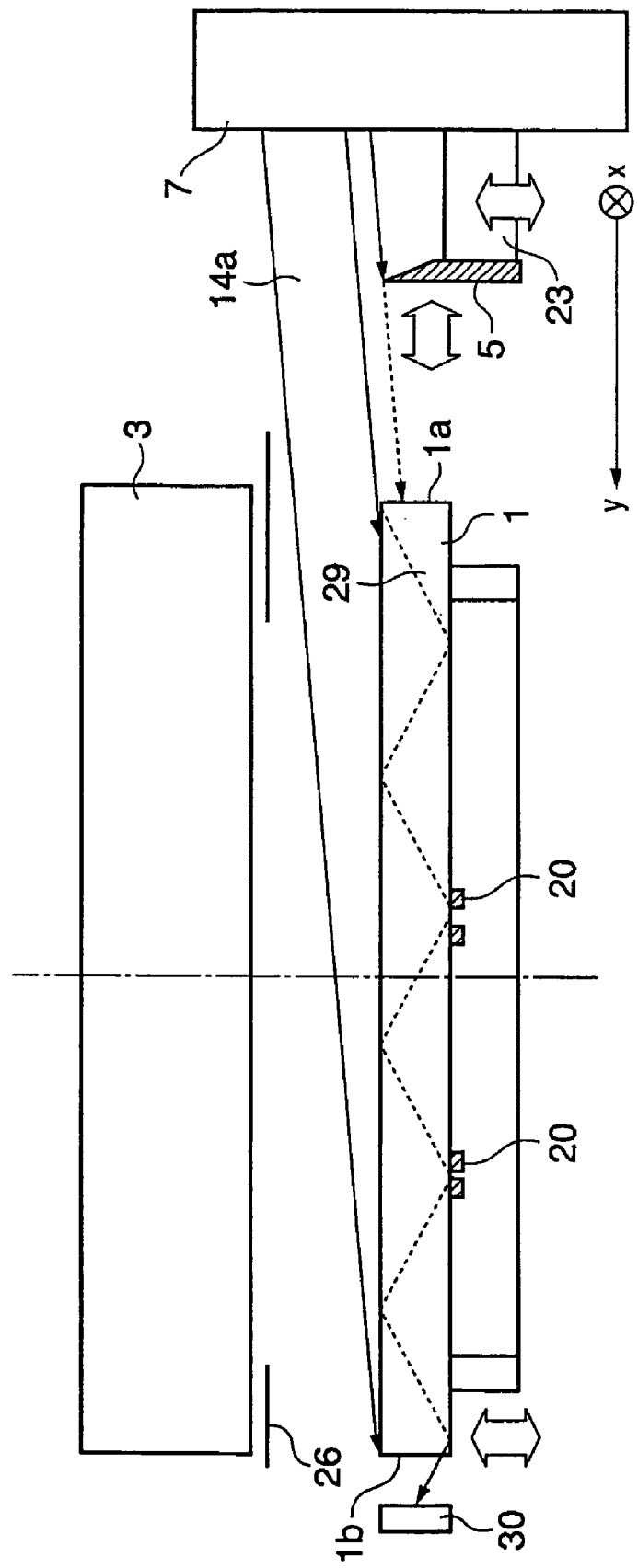
FIG. 7 is a side view showing an outline of the structure of a particle inspection apparatus according to the fourth embodiment when viewed from the x direction.

FIG. 7 is a side view showing an outline of the structure of a particle inspection apparatus according to the fourth embodiment when viewed from the x direction, and a structure on the pellicle 2 side is omitted.

Referring to FIG. 7, an inspection light beam 29, which comes from the edge portion of an end face 1a of a reticle 1 and enters the reticle 1, is repeatedly subjected to total reflection in the reticle 1, and emitted outside from an opposing face 1b. At this time, if an inspection light beam 14a is not applied to the edge portion, the intensity of light emitted from the opposing face 1b decreases. In this embodiment, therefore, a detector 30 is arranged on the opposing face 1b to detect the emitted light amount. Hence, the position of a shield 5 is corrected to prevent the inspection light beam 14a from entering the reticle 1.

More specifically, the detector 30 is arranged on the opposing face 1b of the reticle 1 to detect the amount of the inspection light beam 29 transmitted through the interior of the reticle 1. Information about the light amount detected by the detector 30 is sent to a controller (not shown) to cause a position adjustment mechanism 23 to correct the position of the shield 5. The reticle 1 may be relatively displaced with respect to the shield 5.

According to this embodiment, it is possible to determine, in accordance with the light amount detected by the detector, whether the inspection light beam 14a has entered from the edge portion. Hence, the validity of a particle inspection result can be determined in accordance with the light amount to obtain a highly reliable detection result.

Fifth Embodiment

Figure 8:
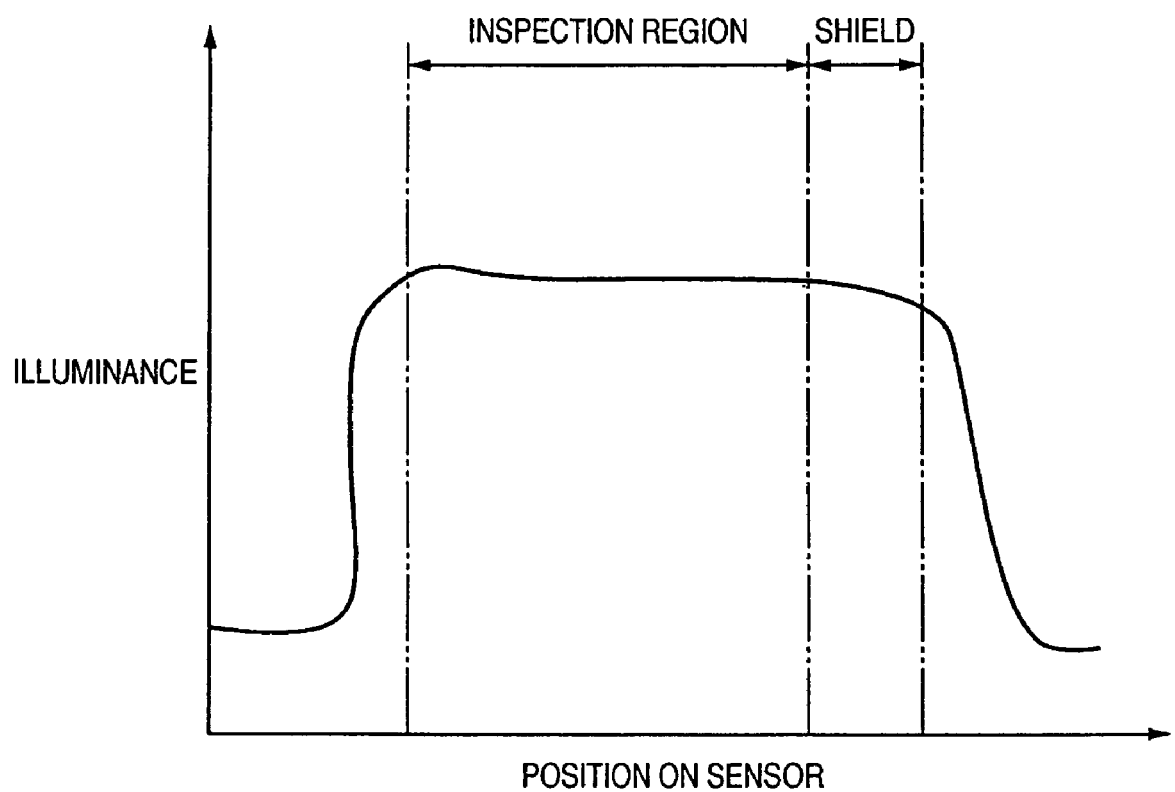
FIG. 8 is a graph showing the illuminance distribution of inspection light along the direction of detection on an inspection surface.

FIG. 8 is a graph showing the illuminance distribution of inspection light along the direction of detection on an inspection surface.

FIG. 8 shows an illuminance distribution in which an inspection region is made uniform by an inspection light forming unit.

According to the present invention, a shield is so arranged as to limit the irradiation range of inspection light such that inspection light is prevented from striking an edge portion.

Figure 9A:
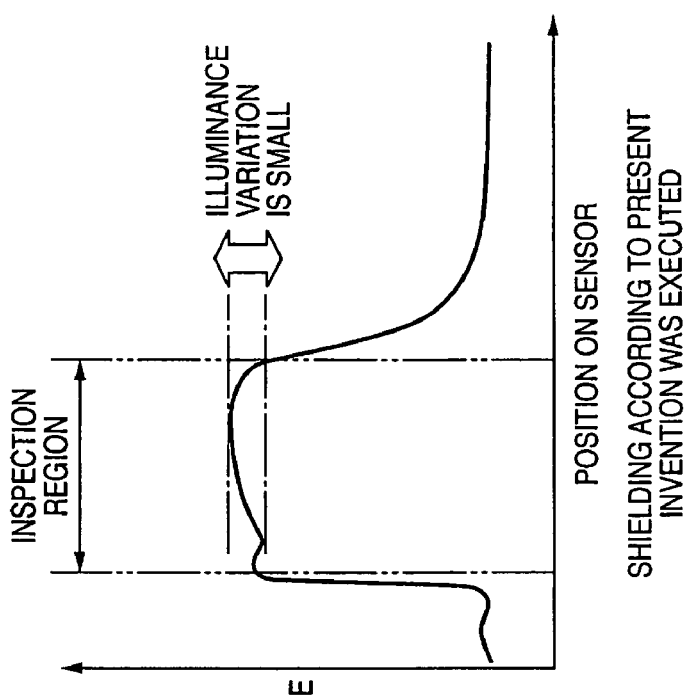
FIGS. 9A and 9B are graphs showing the illuminance distribution of inspection light along the direction of detection on the inspection surface.
Figure 9B:
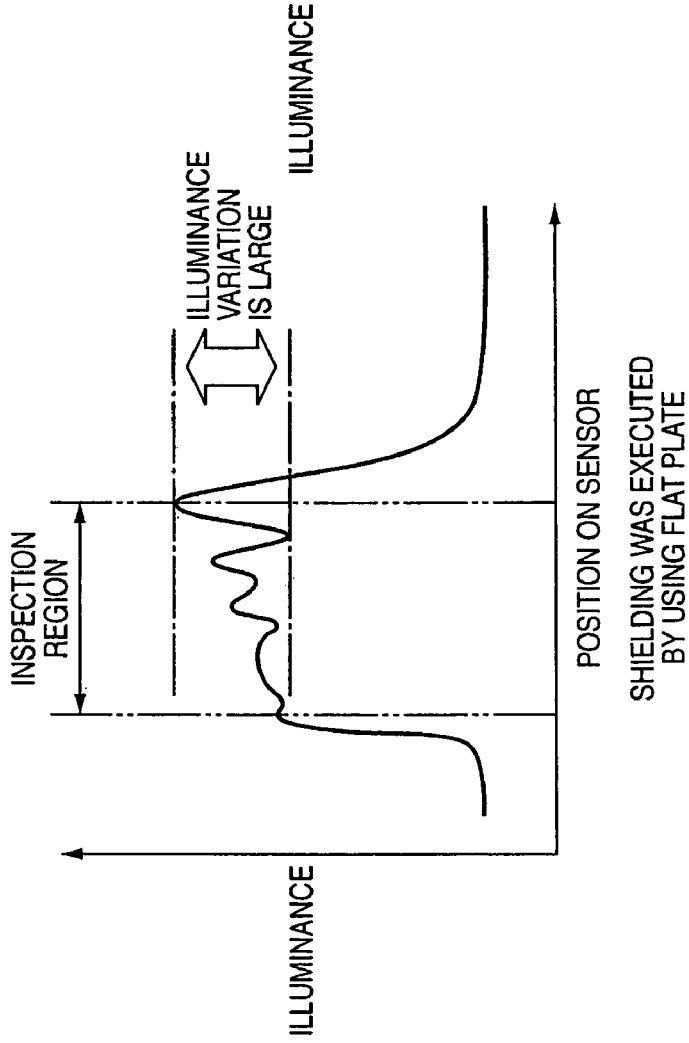
Figure 11A:
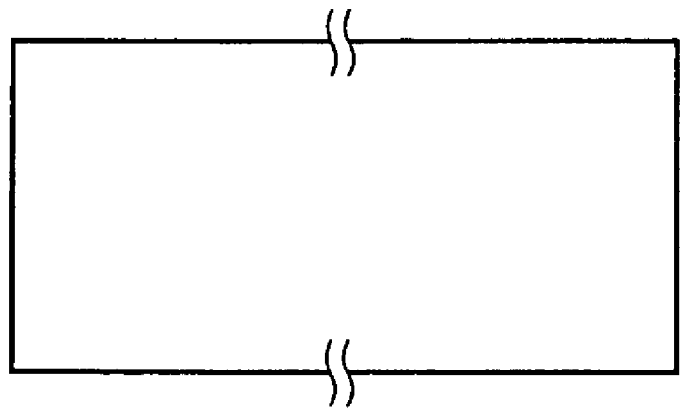
FIGS. 11A and 11B are views showing the shapes of shields.

When a flat shield like FIG. 11A shields inspection light, diffraction light is generated from a shield 5 and illuminance varies in an inspection surface, as shown in FIG. 9A.

Diffraction light generated by a shield has a high intensity in a direction normal to the shield. When the shield 5 is arranged such that a normal to the shield 5 is not parallel to an inclination β [deg] of a detector 3 as shown in FIG. 10, the influence of the diffraction light can be reduced.

Figure 10:
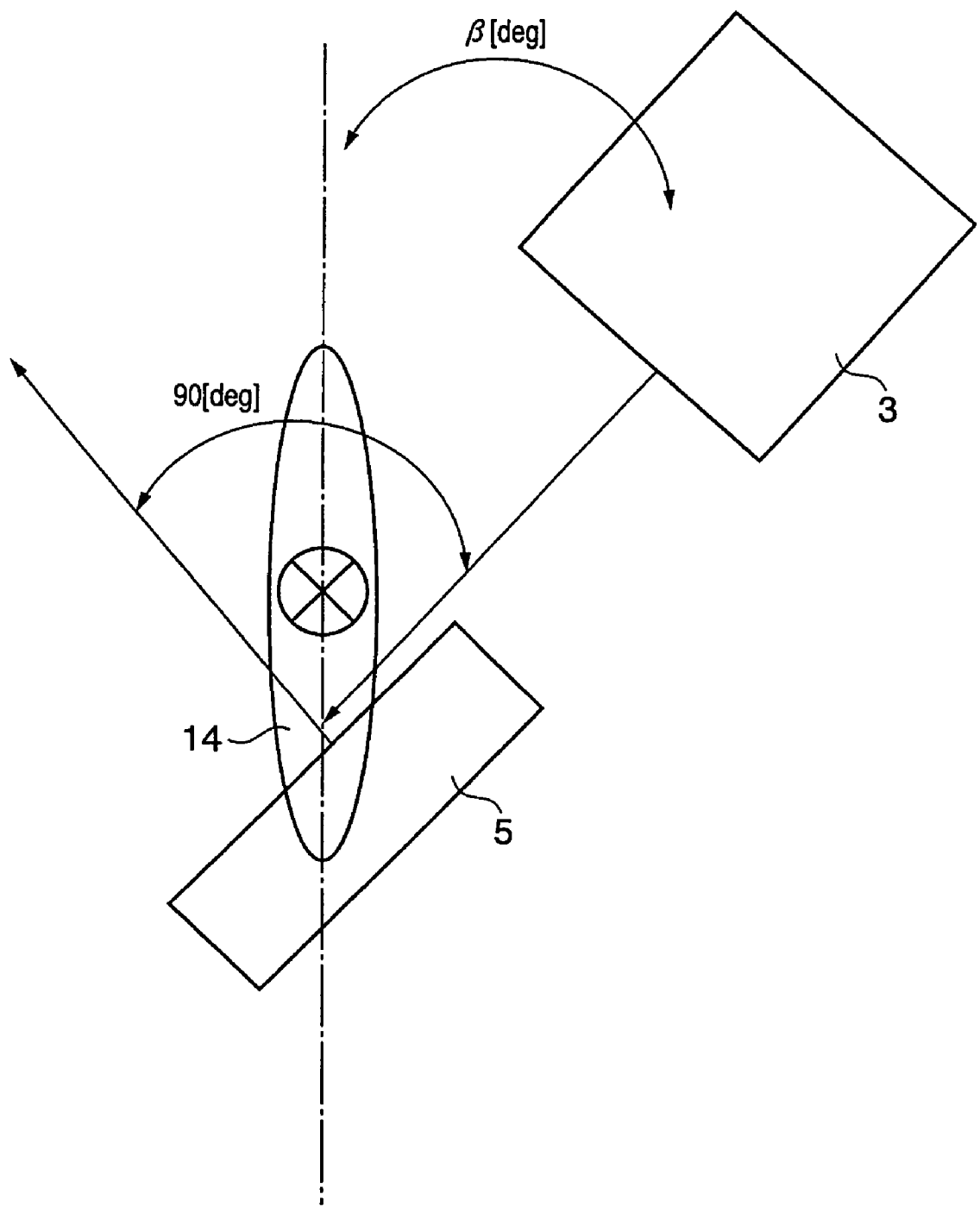
FIG. 10 is a view showing the positional relationship among an inspection light beam, a detector, and a shield.

As described with reference to FIG. 1, an inspection light beam is emitted from a semiconductor laser such as a laser diode serving as a light source, and collimated by a collimator lens 9 to have an elliptical sectional shape as shown in FIG. 10. If the shield 5 is arranged obliquely with respect to the inspection light beam, a region used to shield the inspection light beam varies depending on the minor axis direction of the inspection light beam. As a result, the light amount of the shield slightly varies on an inspection surface. For this reason, there is a possibility that the edge portion cannot be shielded effectively.

Figure 11B:
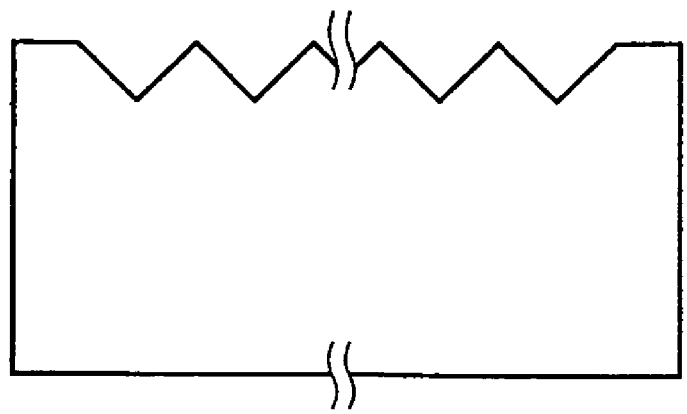

To solve this problem, the present invention employs a saw-toothed shield shown in FIG. 11B. The saw-toothed shield allows positions used to shield inspection light to exist within the saw-tooth depth while suppressing the influence of diffraction light. This makes it possible to suppress a variation in shielding positions.

When the saw-tooth angle is set to be almost perpendicular to the inclination direction of the detector 3, interference can be prevented effectively. In the example shown in FIG. 11B, saw-teeth having a depth of 0.15 mm are formed at an angle of 45°.

[Application Example to an Exposure Apparatus]

Figure 14:
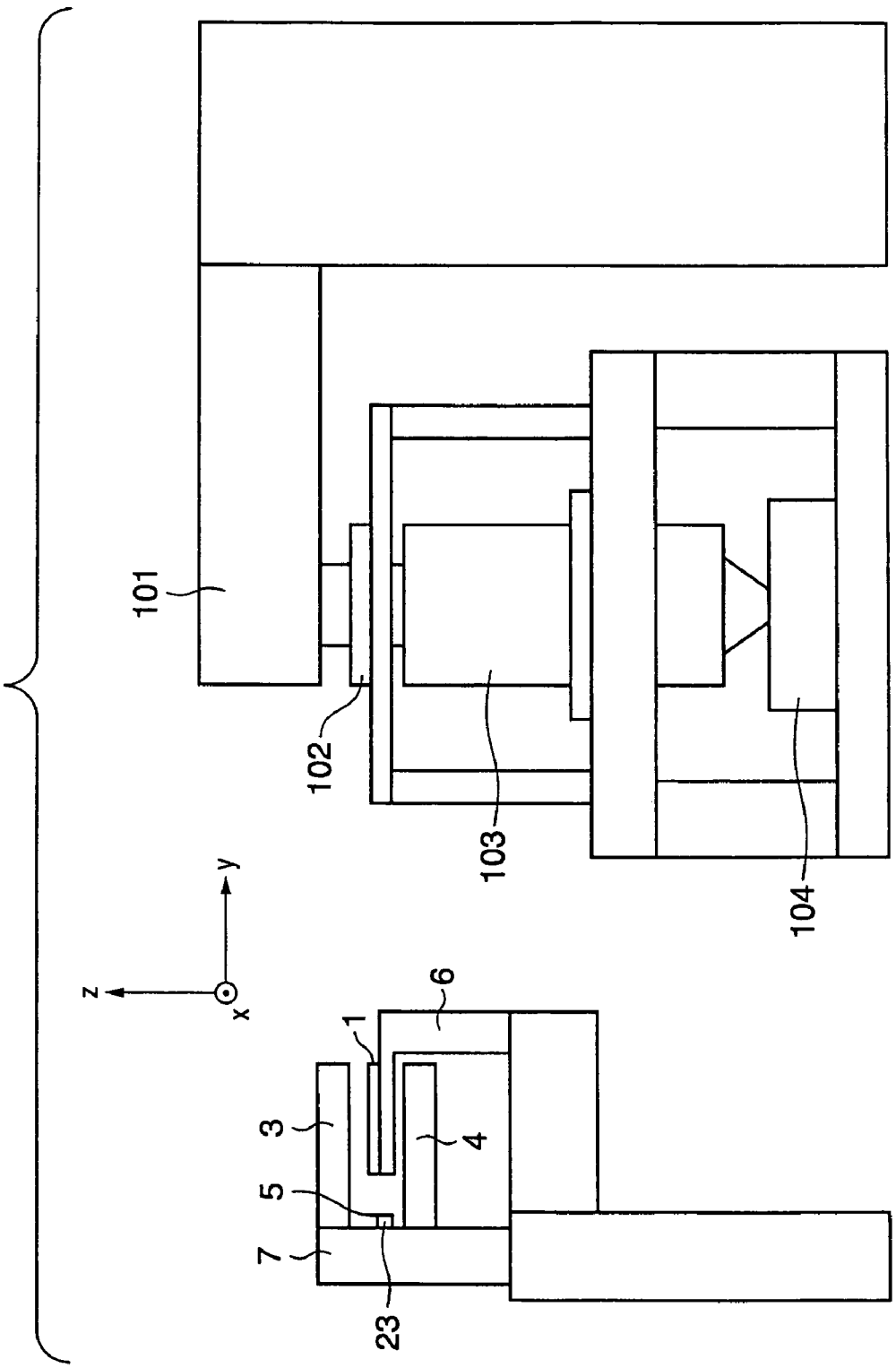
FIG. 14 is a view showing an application example to an exposure apparatus.

FIG. 14 is a view illustrating a semiconductor device manufacturing exposure apparatus in which the particle inspection apparatus according to the above embodiment is mounted.

As shown in FIG. 14, the particle inspection apparatus according to this embodiment is installed near the exposure apparatus to have an inspection table 6 on which a reticle 1 (pellicle 2) before exposure is placed. The particle inspection apparatus causes detectors 3 and 4 and inspection light forming unit 7 to scan in the x direction, thereby detecting the presence/absence of a particle. If a particle is absent as a result of the particle inspection process, the reticle 1 is transported from the particle inspection apparatus onto a reticle stage 102 by a transport robot (not shown).

The exposure apparatus according to this embodiment includes an illumination apparatus 101 which illuminates exposure light, the reticle stage 102 which holds/moves a reticle, a projection optical system 103, and a wafer stage 104 which holds/moves a wafer. The exposure apparatus projects and forms by exposure a circuit pattern formed on a reticle onto a wafer (substrate). The projection exposure method can employ the step and repeat scheme or a step and scan scheme.

The illumination apparatus 101 illuminates a reticle on which a circuit pattern is formed, and includes a light source unit and an illumination optical system. The light source unit uses, for example, a laser as a light source. As the laser, there is available an ArF excimer laser having a wavelength of 193 nm, a KrF excimer laser having a wavelength of 248 nm, or an $F_2$ excimer laser having a wavelength of about 153 nm. However, the laser type is not limited to an excimer laser, and, for example, a YAG laser may be used. Also, the number of lasers is not limited. If a laser is used as the light source, a beam shaping optical system, which shapes a parallel light beam from the laser light source into a desired beam shape, or an incoherent optical system, which converts a coherent laser beam into an incoherent one, is preferably used. A light source usable as the light source unit is not limited to a laser, and one or a plurality of mercury lamps or xenon lamps can be used. The illumination optical system illuminates a reticle, and includes a lens, mirror, light integrator, and field stop.

As the projection optical system 103, there is available an optical system including only a plurality of lens elements, an optical system including a plurality of lens elements and at least one concave mirror (catadioptric optical system), an optical system including a plurality of lens elements and at least one diffraction optical element such as a kinoform, or an optical system of a total reflection mirror type.

Such an exposure apparatus can be used to manufacture a semiconductor device, such as a semiconductor integrated circuit, or a device such as a micromachine or thin-film magnetic head on which a micropattern is formed.

[Device Manufacturing Method]

An embodiment of a device manufacturing method using the exposure apparatus described above will be described next.

FIG. 15 shows the flow of manufacturing a microdevice (e.g., a semiconductor chip, such as an IC or LSI, a liquid crystal panel, a CCD, a thin-film magnetic head, a micromachine, or the like). In step S1 (circuit design), a semiconductor device circuit is designed. In step S2 (exposure control data creation), exposure control data of the exposure apparatus is created based on the designed circuit pattern. In step S3 (wafer fabrication), a wafer is fabricated by using a material such as silicon. In step S4 (wafer process), called a pre-process, an actual circuit is formed on the wafer by lithography using the wafer and the exposure apparatus which has received the prepared exposure control data. Step S5 (assembly), called a post process, is the step of forming a semiconductor chip by using the wafer fabricated in step S4, and includes an assembly process (dicing and bonding) and a packaging process (chip encapsulation). In step S6 (inspection), the semiconductor device manufactured in step S5 undergoes inspections such as an operation confirmation test and a durability test. After these steps, the semiconductor device is completed and shipped (step S7).

Figure 16:
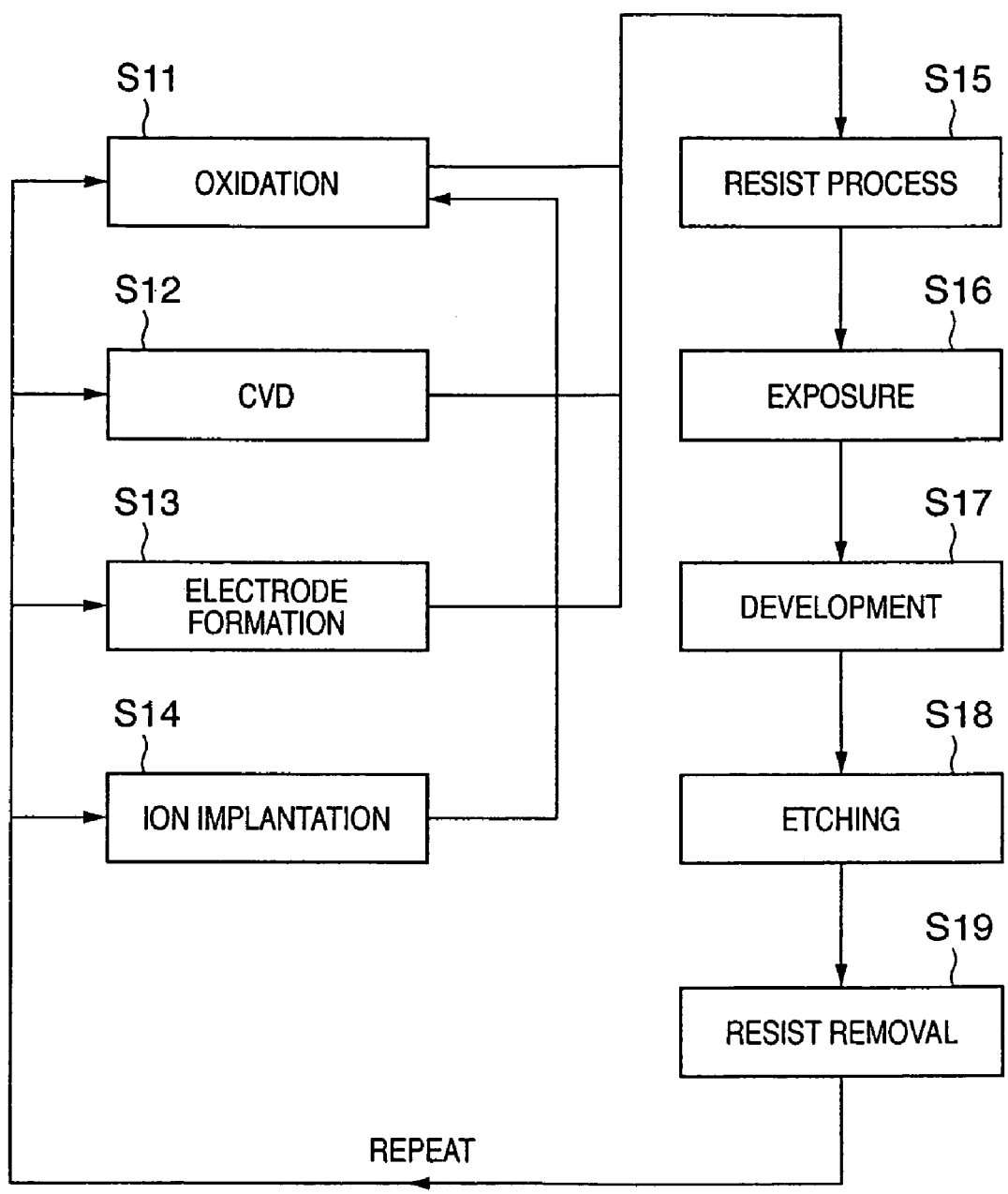
FIG. 16 is a flowchart for explaining a wafer process.

FIG. 16 shows the detailed flow of the wafer process. In step S11 (oxidation), the wafer surface is oxidized. In step S12 (CVD), an insulating film is formed on the wafer surface. In step S13 (electrode formation), an electrode is formed on the wafer by vapor deposition. In step S14 (ion implantation), ions are implanted in the wafer. In step S15 (resist process), a photosensitive agent is applied to the wafer. In step S16 (exposure), the above-mentioned exposure apparatus exposes the wafer to form a circuit pattern. In step S17 (development), the exposed wafer is developed. In step S18 (etching), portions other than the developed resist image are etched. In step S19 (resist removal), any unnecessary resist remaining after etching is removed. These steps are repeated to form multiple circuit patterns on the wafer.

The manufacturing method of the embodiment can manufacture at low cost a high-integration-degree semiconductor device, which is difficult to manufacture by using the prior art techniques.

INDUSTRIAL APPLICABILITY

The present invention can be applied to various precision processing apparatuses and various precision measurement apparatuses, in addition to semiconductor exposure apparatuses used to manufacture a semiconductor element, a liquid-crystal display device, and the like. The present invention is effective to detect a particle on the inspection surface of a processing target or a measurement target.

As many apparently widely different embodiments of the present invention can be made without departing from the spirit and scope thereof, it is to be understood that the invention is not limited to the specific embodiments thereof except as defined in the appended claims.

This application claims the benefit of Japanese Patent Application No. 2005-122945, filed on Apr. 20, 2005, which is hereby incorporated by reference herein in its entirety.

What is claimed is:

1. An inspection apparatus for inspecting a surface of an object for a particle, said apparatus comprising:
   an irradiator configured to irradiate the surface with inspection light;
   a detector configured to detect light scattered at the surface;
   a shield configured to limit an irradiation region of the inspection light emitted by said irradiator; and
   a field stop arranged between the detector and the surface and having an aperture which allows the light scattered at an edge portion of an end face of the object to pass through,
   wherein the light passing through the aperture is detected.

2. An apparatus according to claim 1, wherein said shield includes a sawtooth edge.

3. An apparatus according to claim 1, wherein the light passing through the aperture is detected by said detector.

4. An apparatus according to claim 1, further comprising:
    a mechanism configured to move said shield; and
    a controller configured to control said mechanism based on a detection of the light passing through the aperture.

5. An exposure apparatus for exposing a substrate to light via a reticle, said apparatus comprising:
    an inspection apparatus as defined in claim 1 for inspecting a surface of an object for a particle.

6. An apparatus according to claim 5, wherein said inspection apparatus is configured to inspect a surface of at least one of the reticle and a pellicle for a particle.

7. A method of manufacturing a device, said method comprising steps of:
    exposing a substrate to light via a reticle using an exposure apparatus as defined in claim 5;
    developing the exposed substrate; and
    processing the developed substrate to manufacture the device.

8. An inspection method of inspecting a surface of an object for a particle, said method comprising:
    an emission step of emitting inspection light;
    a first detection step of detecting light passing through an aperture of a field stop arranged between the surface and a detector which detects light scattered from a particle on the surface, the aperture allowing the light scattered at an edge portion of an end face of the object to pass through;
    an adjustment step of adjusting a shield which limits an irradiation region of the emitted inspection light based on a detection of the light passing through the aperture in said first detection step;
    a shield step of shielding the inspection light with the shield to limit an irradiation region of the emitted inspection light; and
    a second detection step of detecting light scattered from a particle on the surface using the detector.

9. A method according to claim 8, wherein the shield includes a sawtooth edge.

* * * * *